(12) United States Patent
Pohjala et al.

(10) Patent No.: US 6,326,363 B1
(45) Date of Patent: Dec. 4, 2001

(54) METHYLENEBISPHOSPHONIC ACID DERIVATIVES

(75) Inventors: Esko Pohjala, Tampere; Heikki Nupponen, Kangasala; Leena Laurén, Turku; Ritva Hannuniemi, Kuusisto; Jouko Vepsäläinen, Kuopio; Jouni Kähkönen, Jyväskylä ; Tomi Järvinen; Marko Ahlmark, both of Kuopio, all of (FI)

(73) Assignee: Leiras Oy, Turku (FI)

( * ) Notice: Subject to any disclaimer, the term of this patent is extended or adjusted under 35 U.S.C. 154(b) by 0 days.

(21) Appl. No.: 09/529,826

(22) PCT Filed: Oct. 20, 1998

(86) PCT No.: PCT/FI98/00814

§ 371 Date: Jul. 12, 2000

§ 102(e) Date: Jul. 12, 2000

(87) PCT Pub. No.: WO99/20634

PCT Pub. Date: Apr. 29, 1999

(30) Foreign Application Priority Data

Oct. 20, 1997 (FI) ........................................................ 974001

(51) Int. Cl.⁷ ................................ C07F 9/38; C07F 9/40; C07F 9/44; A61K 31/66
(52) U.S. Cl. ............................ 514/103; 514/104; 558/153
(58) Field of Search ............................. 558/153; 514/103, 514/104

(56) References Cited

U.S. PATENT DOCUMENTS

| 4,447,256 | 5/1984 | Suzuki et al. ............................. 71/86 |
| 5,462,932 | 10/1995 | Brenner et al. ........................ 514/108 |

FOREIGN PATENT DOCUMENTS

| A3002733 | 7/1979 | (EP) . |
| 0282320 A1 | 9/1988 | (EP) . |
| 0337706 A1 | 10/1989 | (EP) . |
| 0356866 A3 | 3/1990 | (EP) . |
| A3416689 | 3/1991 | (EP) . |
| A1508687 | 10/1992 | (EP) . |
| 0566535 B1 | 10/1993 | (EP) . |
| A1-9015806 | 12/1990 | (WO) . |
| A1-9211267 | 7/1992 | (WO) . |
| A1-9211269 | 7/1992 | (WO) . |
| a1-9211268 | 7/1992 | (WO) . |
| WO-9418216 | * 8/1994 | (WO) . |

OTHER PUBLICATIONS

STN International, CAPLUS Database, Chemical Abstracts Service, (Colubus, Ohio), No. 1987:400258; Cusack, Noel J. et al. Br. J. Pharmacol., 90(4), 791–5 (1987).*

* cited by examiner

Primary Examiner—Deborah C. Lambkin
Assistant Examiner—Andrea M. D'Souza
(74) Attorney, Agent, or Firm—Birch, Stewart, Kolasch & Birch, LLP

(57) ABSTRACT

The object of the invention are novel halogen substituted methylenebisphosphonic acid anhydrides, ester anhydrides, amide anhydrides, and ester amide anhydrides, processes for the preparation of these novel compounds, as well as pharmaceutical preparations comprising these novel compounds.

5 Claims, No Drawings

METHYLENEBISPHOSPHONIC ACID DERIVATIVES

This application is the national phase under 35 U.S.C 0 371 of PCT International Application No. PCT/FI98/00814 which has an International filing date of Oct. 20, 1998, which designated the United States of America.

The object of the present invention are novel methylenebisphosphonic acid derivatives, especially novel halogen substituted methylenebisphosphonic acid anhydrides, ester anhydrides, amide anhydrides and ester amide anhydrides, processes for the preparation of these novel compounds, as well as pharmaceutical preparations comprising these novel compounds.

According to the invention it has been found that the novel methylenebisphosphonic acid anhydrides, ester anhydrides, amide anhydrides, ester amide anhydrides and partial anhydrides as well as their salts in several cases exhibit clearly better properties than the corresponding bisphosphonic acids, their partial ester, partial amide and partial ester amide derivatives, due to the better kinetics and usability of anhydride derivatives, wherefore they have a more controlled effect on the metabolism and functions of the body.

The basic problem with all known methylenebisphosphonates, which are used only as salts of the tetra acid forms, is their poor absorption during oral administration. Thus the dose needed has to be larger.

Absorption and effectiveness may be influenced either by treating the substituents of the intermediate carbon or by changing the groups attached on the phosphorous. Several examples of the improvement of the properties of bisphosphonates by changing the substituents on the intermediate carbon are found in literature (Bisfosfonate on Bones, ed. Bijvoet, Fleisch and Russel, Elsevier, Amsterdam 1995). The absorption of bisphosphonates in tetra acid or salt form or patient compliance have also been tried to improve by formulatory means (CA 2120538, EP 407345, EP 550385, EP 566535, U.S. Pat. No. 5,462,932, WO 9321907, WO 9412200, WO 9426310, WO 9508331, WO 9528145, WO 9529679, WO 9531203), but the improvement on effectiveness has been only marginal in proportion to the dose. However, the phosphorous part has been used for regulation only in few cases. Typically such regulators in the phosphorous part have been partial esters, ester amides, and amides. The anhydride derivatives, which are the subject of the invention, are characterized by a desired selective and controlled effect, which means a better therapeutical index.

Methylenebisphosphonic acids, their salts, tetraesters, amide esters, partial esters and partial ester amides have been disclosed in several publications, but the anhydride derivatives which are the subject of the invention, have not been mentioned in literature nor have their properties been known.

The preparation of methylenebisphosphonic acid tetraesters has been disclosed in the publications U.S. Pat. No. 4,447,256; DE 28 31 578; EP 337 706; EP 282 320; EP 356 866; J. Am. Chem. Soc. 78 (1956) 4450; J. Chem. Soc. 1959, 2272; J. Am. Chem. Soc. 84 (1962) 1876; J. Org. Chem. 35 (1970) 3149; J. Org. Chem. 36 (1971) 3843, Phosphorus, Sulfur and Silicon 42 (1989) 73, J. Chem. Soc. Perkin Trans. 2, (1992) 835 and Phosphorus, Sulfur and Silicon 70 (1992) 182 (mixed tetraesters). The preparation of tetra amide esters has been disclosed in publications J. Organomet. Chem. 304 (1986) 283; Tetrahedron Lett. 26 (1985) 4435 and Acta Chem. Scand. 51 (1997) 932.

The preparation of partial esters has been disclosed in publications WO 9015806, WO 9211267, WO 9221169, Tetrahedron Lett., 34 (1993) 4551, Tetrahedron 51 (1995) 6805 and Tetrahedron Lett. 37 (1996) 3533, and the preparation of partial amides and partial amide esters has been disclosed in the patent publication WO 9211268.

Mono or bisphosphonate parts can be added to a known medicinal substance inseparably or as a pro-part, and thus increase targeting to the bone of the latter, when the same is used for the treatment of bone diseases or for increasing the solubility of a poorly water-soluble drug into water phase. Also some mixed anhydrides of mainly phosphoric acid and carboxylic acid are known for this purpose.

The novel molecules according to the present invention, which contain an acid anhydride group as a pro-part or are active as such, are very suitable for the treatment of disorders relating to the metabolism of calcium and other, especially bivalent metals. They can be used in the treatment of both bone diseases, especially bone formation and resorption disorders, such as osteoporosis and Paget's disease, and also diseases in the soft tissues, such as deposition, mineralisation conditions and ossification disorders.

On the other hand, being pyrophosphate analogs, the novel anhydride derivatives of methylenebisphosphonic acids are suitable for the treatment of disorders in the pyrophosphate functions of the organism, including those functions, wherein an active, but disturbance-prone or incorrectly functioning organic part is coupled to (pyro) phosphate or acts as a metal complex or as a combination of the latter.

The novel bisphosphonates regulate either directly or via an indirect mechanism the quality and level of both cations and/or pyrophosphate compounds, which are freely present in the body fluids or bind to tissues, are active in tissues and are liberated therefrom, i.e. formations, dissolutions, couplings and eliminations. Thus they are able to regulate cellular metabolism, growth and destruction.

Based on the above, they can be used for example in the treatment of bone cancer and its metastases, ectopic calcifications, urolithiasis, rheumatoid arthritis, osteitides and bone degenerations.

The invention concerns novel methylenebisphosphonic acid derivatives of the general formula I

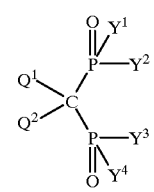

(I)

wherein $Y^1$, $Y^2$, $Y^3$ and $Y^4$ are a group $OR^1$, $NR^2R^3_1$, $OCOR^1$, $OCNR^2R^3$, $O(CO)OR^1$, $O(SO_2)R^1$, $O(SO_2)OR^1$ or $OP(O)R^2(OR^3)$, wherein $R^1$, $R^2$ ja $R^3$ are independently of each other hydrogen, straight or branched, optionally substituted, optionally unsaturated $C_1$–$C_{22}$ alkyl, optionally substituted, optionally unsaturated $C_3$–$C_{10}$ cycloalkyl, heterocyclyl, aryl, heteroaryl, aralkyl or silyl $SiR_3$, wherein R means a $C_1$–$C_4$ alkyl, phenyl, a substituted phenyl or combinations of $C_1$–$C_4$ alkyls and/or phenyls, or the groups $R^2$ and $R^3$ together with the adjacent nitrogen atom form a 3 to 10-membered saturated, partly saturated or aromatic ring, wherein in addition to the nitrogen atom there may be one or two heteroatoms selected from the group N, O and S, or the groups $R^2$ and $R^3$ together with the adjacent O-PO-O group form a 5 or 6-membered ring, with the proviso that in the formula I at least one of the groups $Y^1$, $Y^2$, $Y^3$ and $Y^4$ is other than a group $OR^1$ or $NR^2R^3$;

$Q^1$ and $Q^2$ are independently of each other hydrogen, fluorine, chlorine, bromine or iodine, including the stereoisomers, such as geometrical isomers and optically active isomers, of the compounds, as well as the pharmacologically acceptable salts of these compounds.

Optionally unsaturated $C_1$–$C_{22}$ alkyl as a group $R^1$, $R^2$ and $R^3$ means alkyl, alkenyl or alkynyl, which contain independently of each other 1 to 22, respectively 2 to 22 carbon atoms, preferably 1 to 8, respectively 2 to 8 carbon atoms, and most preferably 1 to 5, respectively 2 to 5 carbon atoms.

Optionally unsaturated $C_3$–$C_{10}$ cycloalkyl as a group $R^1$, $R^2$ and $R^3$ means cycloalkyl or -alkenyl, which contain 3 to 10 carbon atoms, preferably 5 or 6 carbon atoms, and may be unsubstituted or substituted for example with a lower alkyl (1–4 C). Preferably it is cyclopropyl, -butyl, -pentyl or -heptyl or the corresponding cycloalkenyl group. A heterocyclyl contains in its ring one or several heteroatoms from the group N, O and S.

Aryl or aralkyl as a group $R^1$, $R^2$ and $R^3$ means an optionally $C_1$–$C_4$-alkyl, -alkoxy or halogen substituted monocyclic aryl or aralkyl, such as phenyl or benzyl, most preferably, however, an unsubstituted phenyl or benzyl.

When in the silyl group $SiR_3$ the group R is a lower alkyl containing 1 to 4 C-atoms, it is especially methyl, ethyl, isopropyl, butyl or t-butyl. When the group R in the silyl group means combinations of $C_1$–$C_4$-alkyls or phenyls, it is for example dimethyl t-butyl, methyldiisopropyl, dimethylphenyl, diethylphenyl, methyl t-butyl phenyl or diisopropyl-(2,6-dimethylphenyl).

When $R^2$ and $R^3$ together with the nitrogen atom form a heterocyclic saturated ring, this ring is typically for example morpholinyl, tiomorpholinyl, piperidinyl, piperazinyl, azetidinyl, aziridinyl or pyrrolidinyl, or when they form a partly saturated or aromatic ring, the ring is for example pyrrolyl, imidazolyl, triazolyl, tetrazolyl, oxazolyl, tiazolyl, pyridyl, pyrimidyl, pyrazinyl, pyridazinyl or azepinyl. This group may be substituted as described above for cycloalkyl, but it is preferably, however, unsubstituted, such as for example pyrrolidinyl, morpholinyl or piperazinyl.

When $R^2$ and $R^3$ together with the adjacent O—PO—O group form a 5 or 6-membered ring, said ring is preferably dioxaphospholaneoxide or dioxaphosphaneoxide.

$Q^1$ and $Q^2$ are most preferably both chlorine.

Salts of the compounds of the formula I are especially their salts with pharmaceutically acceptable bases, such as metal salts, for example alkalimetal salts, especially lithium, sodium and potassium salts, alkaline earth metal salts, such as calcium or magnesium salts, copper, aluminium or zinc salts, as well as ammonium salts formed with ammonia or with primary, secondary or tertiary, both aliphatic and alicyclic as well as aromatic amines, aliphatic or aromatic quaternary ammonium salts, salts with aminoalcohols, such as ethanol-, diethanol- and triethanol amines, tris (hydroxymethyl)aminomethane, 1- and 2-methyl- and 1,1-, 1,2- and 2,2-dimethylaminoethanols, N-mono- and N,N-dialkylaminoethanols, N-(hydroxymethyl and ethyl)-N,N-ethanediamines, as well as amino crown ethers and cryptates, and heterocyclic ammoniumsalts, such as azetidinium, pyrrolidinium, piperidinium, piperazinium, morpholinium, pyrrolium, imidazolium, pyridinium, and quinolinium salts, various tetraalkyl ammonium salts, such as tetramethyl ammonium, methyltributyl ammonium, and benzyldimethyl higher-alkyl ammonium salts.

Preferred compounds according to the invention are methylenebisphosphonic acid derivatives of the formula I, wherein two of the groups $Y^1$, $Y^2$, $Y^3$ and $Y^4$ are a group $OCOR^1$, wherein $R^1$ is as defined above. Especially preferred of these compounds are those, wherein $R^1$ a straight or branched $C_1$–$C_{22}$ alkyl or phenyl.

Preferred compounds according to the invention are also methylenebisphosphonic acid derivatives of the formula I, wherein two of the groups $Y^1$, $Y^2$, $Y^3$ and $Y^4$ are a group $OR^1$, wherein $R^1$ is as defined above. Especially preferred of these compounds are those, wherein $R^1$ is a straight or branched $C_1$–$C_{22}$ alkyl or phenyl.

Further preferred among the compounds of the formula I, wherein two of the groups $Y^1$, $Y^2$, $Y^3$ and $Y^4$ are a group $OCOR^1$ or $OR^1$, are the compounds wherein the third one of the groups $Y^1$, $Y^2$, $Y^3$ and $Y^4$ is selected from the group consisting of alkyl sulphonyl, loweralkyl carboxy, benzoyl, arylsulphonyl, mono- and di-lower alkyl phosphoryl.

Examples of preferred compounds according to the invention are for instance:

P,P'-diacetyl(dichloromethylene)bisphosphonate disodium salt and free acid,

P,P'-dibutyroyl(dichloromethylene)bisphosphonate disodium salt and free acid,

P,P'-di(pivaloyl)(dichloromethylene)bisphosphonate disodium salt and free acid,

P,P'-di(benzoyl)(dichloromethylene)bisphosphonate disodium salt and free acid,

P,P'-di(isobutyroyl)(dichloromethylene)bisphosphonate disodium salt and free acid, P,P'-di(tetradecanoyl)(dichloromethylene)bisphosphonate disodium salt and free acid, P,P'-di(octadecanoyl)(dichloromethylene)bisphosphonate disodium salt and free acid.

The derivatives according to the present invention can be prepared in many different ways, depending on which methylenebisphosphonic acid anhydride is desired to be prepared. The methylenebisphosphonic acids used as starting materials, their salts, tetraesters, tetraester amides, partial esters and partial amide esters can be prepared by known methods (cf. for example WO 92/11267 and WO 92/11268). Thus partial esters can be prepared for example by selectively hydrolysing methylenebisphosphonic acid tetraester, by selectively esterifying bisphosphonic acid, or from other partial esters by intramolecular or intermolecular reactions. Partial amide esters can, on the other hand, be prepared for example by selectively hydrolysing bisphosphonic acid tetra (amideester) or from other partial ester amides by intramolecular or intermolecular reactions.

The compounds according to the present invention wherein the groups $Y^1$, $Y^2$, $Y^3$ and $Y^4$ are either partly (1 to 3 groups) or all other substituents defined above for these groups than the groups $OR^1$ or $NR^2R^3$, can be prepared according to the alternative a) of the scheme 1 by stage-by-stage substitution reactions from the corresponding methylenebisphosphonic acids or their salts. The starting material (II), wherein at least one of the groups $X^1$–$X^4$ or all are independently of each other OH or OM, wherein M may be a metal or ammonium group, is selectively reacted with a desired acid derivative (Z-A), e.g. with an acid chloride.

The same method can be applied according to the alternative b) of the scheme 1, when at least one of the groups $X^1$–$X^4$ or all of them are halogens or halogen analogs, respectively, such as sulphonyloxy, by letting this compound react with selected acid(s) (A-OH) or its metal salt (A-OM) and finally by removing extra groups X and eventually extra groups Y, e.g. by hydrolysing with water. If these extra, especially halogen-containing groups are changed by adding alcohol, thiol or amine to the mixture, mixed ester, ester amide, or amide ester anhydrides are obtained.

Scheme 1:

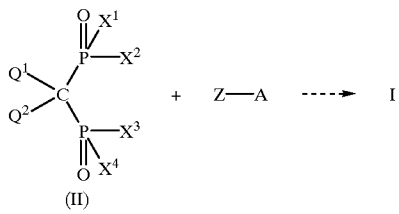

(II)

a) $X^n$ (n=1–4)=OH or OM, wherein M is a metal or ammonium group; $Q^1$ ja $Q^2$ have the same meanings as above; Z is halogen or analog; A means a group $OCOR^1$, $OCONR^2R^3$, $O(CO)OR^1$, $O(SO_2)R^1$, $O(SO_2)OR^1$ or $OP(O)R^2(OR^3)$ wherein $R^1$, $R^2$ and $R^3$ mean the same as above; or b) $X^n$ (n=1–4)=halogen or analog; Z is OH or OM, wherein M is a metal or ammonium group; and A, $Q^1$ and $Q^2$ have the same meanings as above.

From the tetraderivatives I prepared as described above one can further prepare c) by selective hydrolysis tri-, di- and mono partial anhydride derivatives I according to the scheme 2:

Scheme 2:

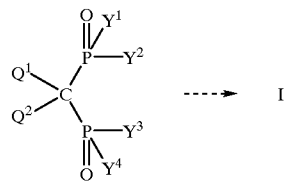

C) $Y^n$ (n=4)=A→$Y^n$ (n=1–3)=A, wherein A has the same meanings as above in scheme 1.

The progress of hydrolysis can be followed either chromatographically or with the help of $^{31}$P-NMR spectroscopy. The reaction may be interrupted when the concentration of the desired partial anhydride (at least one of the groups Y=OH or OM) is at its highest, and the product may be isolated from the reaction mixture either as an acid or salt by precipitation, extraction or chromatographically.

Mixed ester, ester amide or amide ester anhydrides can especially be prepared by starting from a molecule according to the formula I, wherein groups $Y^1$, $Y^2$, $Y^3$ or $Y^4$ represent a selected amount of the above mentioned groups X or other groups defined for Y than $OR^1$ or $NR^2R^3$. This may react according to the method a with a suitable acid halide or according to the method b with an acid or its metal salt.

The novel compounds according to the invention can be administered enterally or parenterally. All the conventional administration forms, such as tablets, capsules, granules, syrups, solutions, implants and suspensions, come into question. Also all pharmaceutically acceptable formulation, dissolution and administration adjuvants, as well as stabilizing agents, viscosity regulators, dispergants and buffers, may be used.

Suitable adjuvants include i.a. tartrate and citrate buffers, alcohols, EDTA and other non-toxic complexing agents, solid and liquid polymers and other sterile substrates, starch, lactose, mannitol, methylcellulose, talc, silicic acids, fatty acids, gelatine, agar-agar, calcium phosphate, magnesium stearate, animal and vegetable fats and, if desired, flavouring and sweetening agents.

The dosage depends on several factors, for example on the manner of administration, species, age and individual condition. The daily doses are approximately 1 to 1000 mg, usually 10 to 200 mg per person, and they can be administered as a single dose or may be divided into several doses.

In the following, the composition of a typical capsule and tablet is given:

| Capsule | mg/capsule |
|---|---|
| Active agent | 100.0 mg |
| Starch | 20.0 mg |
| Magnesium stearate | 1.0 mg |

| Tablet | mg/tablet |
|---|---|
| Active agent | 400.0 mg |
| Microcrystalline cellulose | 20.0 mg |
| Lactose | 67.0 mg |
| Starch | 10.0 mg |
| Talc | 4.0 mg |
| Magnesium stearate | 1.0 mg |

The compounds of the invention may be prepared also into an intramuscularly or parenterally administrable preparation, for example an infusion concentrate, wherein as adjuvants e.g. sterile water, phosphate buffer, sodium chloride, sodium hydroxide, hydrochloric acid or other suitable pharmaceutically acceptable ajuvants may be used.

The purpose of the following examples is to illustrate the invention without, however, limiting the same in any way.

EXAMPLE 1

P,P-Dimethyl-P'-methanesulphonyl(dichloromethylene) bisphosphonate Methyltributylammonium Salt and Free Acid 12.2 g (0.025 moles) of trimethyl(dichloromethylene) bisphosphonate methyltributylammonium salt and 2.9 g (0.025 moles) of mesyl chloride are dissolved in 150 ml of anhydrous acetonitrile and the solution is stirred for about 20 min under reflux. The progress of the reaction is followed with $^{31}$P-NMR. Solvent is evaporated under vacuum and about 13.2 g (96% of the theoretical) of yellow, oily P,P-dimethyl-P'-methanesulphonyl(dichloromethylene) bisphosphonate methyltributylammonium salt ($^{31}$P-NMR (CDCl$_3$): 13.12 ppm (P), −2.42 ppm (P'), $^2J_{PP'}$=20.3 Hz, $^3J_{PH}$=10.7 Hz), is obtained, the concentration of which is 99.5% and wherefrom the corresponding acid can be liberated with acid treatment.

For instance the following methylenebisphosphonate P,P-diester-P'-monoanhydrides and their quaternary ammonium salts can be prepared analogously:

P,P-Dimethyl-P'-pivaloyl(dichloromethylene) bisphosphonate methyltributyl ammonium salt, $^{31}$P-NMR (CDCl$_3$): 15.13 ppm (P), −0.63 ppm (P'), $^2J_{PP'}$=18.9 Hz, $^3J_{PH}$=10.7 Hz.

P,P-Dimethyl-P'-pentyl(dichloromethylene) bisphosphonate methyltributyl ammonium salt, $^{31}$P-NMR (CDCl$_3$): 15.12 ppm (P), −1.04 ppm (P'), $^2J_{PP'}$=18.6 Hz, $^3J_{PH}$=10.6 Hz.

P,P-Dimethyl-P'-benzoyl(dichloromethylene) bisphosphonate methyltributyl ammonium salt, $^{31}$P-NMR (CDCl$_3$): 14.87 ppm (P), −0.79 ppm (P'), $^2J_{PP'}$=23.0 Hz, $^3J_{PH}$=10.7 Hz. P,P-Dimethyl-P'-trichloroacetyl(dichloromethylene) bisphosphonate methyltributyl ammonium salt, $^{31}$P-NMR (CDCl$_3$): 14.03 ppm (P), 1.04 ppm (P'), $^2J_{PP'}$=19.9 Hz, $^3J_{PH}$=10.8 Hz.

P,P-Di-isopropyl-P'-pivaloyl(dichloromethylene) bisphosphonate N-isopropylpyridinium salt, $^{31}$P-NMR (CDCl$_3$): 8.99 ppm (P), 0.24 ppm (p'), $^2J_{PP'}$=24.5 Hz, $^3J_{PH}$=6.6 Hz. P,P-Diethyl-P'-methanesulphonyl (dichloromethylene)bisphosphonate ethyltributyl ammonium salt, $^{31}$P-NMR (CDCl$_3$): 9.90 ppm (P), −1.29 ppm (P'), $^2J_{PP'}$=22.8 Hz, $^3J_{PH}$=7.9 Hz.

P,P-Di-isopropyl-P'-methanesulphonyl (dichloromethylene)bisphosphonate N-isopropylpyridinium salt, $^{31}$P-NMR (CDCl$_3$): 7.79 ppm (P), −1.45 ppm (P'), $^2J_{PP'}$=23.3 Hz, $^3J_{PH}$=6.4 Hz.

P-Methyl-P-isopropyl-P'-methanesulphonyl (dichloromethylene)bisphosphonate methyltributyl ammonium salt, $^{31}$P-NMR (CDCl$_3$): 10.80 ppm (P), −2.21 ppm (P'), $^2J_{PP'}$=21.2 Hz, $^3J_{PH}$=6.5 Hz, $^3J_{P'H}$=10.5 Hz.

P,P-Dimethyl-P'-benzenesulphonyl(dichloromethylene) bisphosphonate methyltributyl ammonium salt, $^{31}$P-NMR (CDCl$_3$): 13.07 ppm (P), −2.28 ppm (P'), $^2J_{PP'}$=21.0 Hz, $^3J_{PH}$=10.7 Hz.

P,P-Dimethyl-P'-p-toluenesulphonyl(dichloromethylene) bisphosphonate methyltributyl ammonium salt, $^{31}$P-NMR (CDCl$_3$): 13.27 ppm (P), −2.54 ppm (P'), $^2J_{PP'}$=20.2 Hz, $^3J_{PH}$=10.3 Hz.

P,P-Dimethyl-P'-2,4,6-trimethylbenzenesulphonyl (dichloromethylene)bisphosphonate methyltributyl ammonium salt, $^{31}$P-NMR (CDCl$_3$): 13.53 ppm (P), −2.81 ppm (P'), $^2J_{PP'}$=22.0 Hz, $^3J_{PH}$=10.8 Hz.

P,P-Dimethyl-P'-2,4,6-tri-isopropylbenzenesulphonyl (dichloromethylene)bisphosphonate methyltributyl ammonium salt, $^{31}$P-NMR (CDCl$_3$): 13.54 ppm (P), −2.83 ppm (P'), $^2J_{PP'}$=21.9 HZ, $^3J_{PH}$=10.8 Hz.

P,P-Dimethyl-P'-d-10-camphorsulphonyl (dichloromethylene)bisphosphonate methyltributyl ammonium salt, $^{31}$P-NMR (CDCl$_3$): 13.06 ppm (P), −2.82 ppm (P'), $^2J_{PP'}$=20.7 Hz, $^3J_{PH}$=10.7 Hz.

P,P-Dimethyl-P'-pivaloyl(dibromomethylene) bisphosphonate methyltributyl ammonium salt, $^{31}$P-NMR (CDCl$_3$): 15.16 ppm (P), −0.90 ppm (P'), $^2J_{PP'}$=14.5 Hz, $^3J_{PH}$=10.9 Hz.

P,P-Dimethyl-P'-methanesulphonyl(dibromomethylene) bisphosphonate methyltributyl ammonium salt, $^{31}$P-NMR (CDCl$_3$): 12.99 ppm (P), −2.83 ppm (P'), $^2J_{PP'}$=15.7 Hz, $^3J_{PH}$=10.6 Hz.

P,P-Dimethyl-P'-trichloromethanesulphonyl (dibromomethylene)bisphosphonate methyltributyl ammonium salt, $^{31}$P-NMR (CDCl$_3$): 13.12 ppm (P), −2.98 ppm (p'), $^2J_{PP'}$=15.4 Hz.

P,P-Dimethyl-P'-p-toluenesulphonyl(dichloromethylene) bisphosphonate methyltributyl ammonium salt, $^{31}$P-NMR (CDCl$_3$): 13.13 ppm (P), −2.95 ppm (P'), $^2J_{PP'}$=15.1 Hz, $^3J_{PH}$=10.8 Hz.

P,P-Dimethyl-P'-pivaloyl(monobromomethylene) bisphosphonate methyltributyl ammonium salt, $^3$P-NMR (CDCl$_3$): 20.51 ppm (P), 0.95 ppm (P'), $^2J_{PP'}$=6.0 Hz, $^2J_{PH}$=16.5 Hz, $^3J_{PH}$=10.9 Hz.

P,P-Dimethyl-P'-methanesulphonyl (monobromomethylene)bisphosphonate methyltributyl ammonium salt, $^{31}$P-NMR (CDCl$_3$): 17.46 ppm (P), 1.19 ppm (P'), $^2J_{PP'}$=7.3 Hz, $^3J_{PH}$=17.3 Hz, $^3J_{PH}$=11.0 Hz.

P,P-Dimethyl-P'-acetyl(dichloromethylene) bisphosphonate methyltributyl ammonium salt, $^{31}$P-NMR (CDCl$_3$): 13.71 ppm (P), −4.10 ppm (p'), $^2J_{PP'}$=18.9 Hz.

P,P-Dimethyl-P'-propionyl(dichloromethylene) bisphosphonate methyltributyl ammonium salt, $^{31}$P-NMR (CDCl$_3$): 14.57 ppm (P), −1.61 ppm (P') $^2J_{PP'}$=19.1 Hz, $^3J_{PH}$=10.7 Hz.

P,P-Dimethyl-P'-isovaleroyl(dichloromethylene) bisphosphonate methyltributyl ammonium salt, $^{31}$P-NMR (CDCl$_3$): 14.17 ppm (P), −1.18 ppm (P'), $^2J_{PP'}$=18.3 Hz, $^3J_{PH}$=10.7 Hz.

P,P-Dimethyl-P'-dimethylcarbamoyl(dichloromethylene) bisphosphonate methyltributyl ammonium salt, $^{31}$P-NMR (CDCl$_3$): 14.80 ppm (P), −1.62 ppm (P'), $^2J_{PP'}$=18.2 Hz, $^3J_{PH}$=10.6 Hz.

P,P-Dimethyl-P'-acetyl(dibromomethylene) bisphosphonate methyltributyl ammonium salt, $^{31}$P-NMR (CDCl$_3$): 14.73 ppm (P), −2.00 ppm (P'), $^2J_{PP'}$=13.7 Hz, $^3J_{PH}$=10.8 Hz.

P,P-Dimethyl-P'-propionyl(dibromomethylene) bisphosphonate methyltributyl ammonium salt, $^{31}$P-NMR (CDCl$_3$): 14.17 ppm (P), −1.40 ppm (P'), $^2J_{PP'}$=14.0 Hz, $^3J_{PH}$=10.7 Hz.

P,P-Dimethyl-P'-dimethylcarbamoyl(dibromomethylene) bisphosphonate methyltributyl ammonium salt, $^{31}$P-NMR (CDCl$_3$): 14.92 ppm (P), −1.92 ppm (P'), $^2J_{PP'}$=14.0 Hz.

P,P-Di-isopropyl-P'-acetyl(monochloromethylene) bisphosphonate N-isopropylpyridinium salt, $^{31}$P-NMR (CDCl$_3$): 14.49 ppm (P), 3.07 ppm (P'), $^2J_{PP'}$=8.4 Hz, $^2J_{PH}$=17.1 Hz, $^3J_{PH}$=7.7 Hz.

P,P-Di-isopropyl-P'-pivaloyl(monochloromethylene) bisphosphonate N-isopropylpyridinium salt, $^{31}$P-NMR (CDCl$_3$): 15.02 ppm (P), 3.02 ppm (P'), J$_{PP}$=9.8 Hz, $^2J_{PH}$=17.4 Hz, $^3J_{PH}$=7.1 Hz.

P,P-Di-isopropyl-P'-pivaloyl(bromochloromethylene) bisphosphonate N-isopropylpyridinium salt and P,P-di-isopropyl-P'-methanesulphonyl (bromochloromethylene)bisphosphonate N-isopropylpyridinium salt.

Preparation of starting materials:

The quaternary monoammonium salts of monochloro-, dichloro-, monobromo- or (dibromomethylene) bisphosphonate triesters to be used as starting materials can be prepared for example by treating the corresponding tetraester with one equivalent of a tertiary amine in a dry, inert solvent at a temperature of about 25–100° C., whereby the progress of the reaction can be followed with $^{31}$P-NMR.

The following example illustrates the preparation of starting materials:

30.1 g (0.1 moles) of tetramethyl(dichloromethylene) bisphosphonate is dissolved in 60 ml of anhydrous chloroform and 18.6 g (0.1 moles) of anhydrous tributylamine are added. The solution is mixed under reflux for 4 h and the solvent is evaporated under vacuum. The yield is about 50 g (100% of the theoretical) of almost colourless, oily trimethyl(dichloromethylene) bisphosphonate methyltributyl ammonium salt, the concentration of which is 98%. ($^{31}$P-NM (CDCl$_3$): 15.50 ppm (P), 4.25 ppm (P'), $^2J_{PP'}$=16.6 Hz).

EXAMPLE 2

P,P-Dimethyl-P'-dimethylphosphoryl(dichloromethylene) bisphosphonate Methyltributyl Ammonium Salt and Free Acid 4.86 g (0.01 moles) of trimethyl(dichloromethylene) bisphosphonate methyltributyl ammonium salt is dissolved in 50 ml of anhydrous acetonitrile and 1.45 g (0.01 moles) of dimethylchlorophosphite are added and the solution is stirred under reflux for about 1 h (the progress of the reaction is followed with $^{31}$P-NMR). The solvent is evaporated under vacuum, whereby about 5.6 g (96% of the theoretical) of brownish, oily P,P-dimethyl-P'-dimethylphosphoryl (dichloromethylene)bisphosphonate methyltributyl ammonium salt ($^{31}$P-NMR (CDCl$_3$): 13.90 ppm (P), −4.84 ppm (P'), −10.23 ppm (P"), $^2J_{PP'}$=20.3 Hz, $^2J_{P'P''}$=27.7 Hz, $^3J_{PH}$=10.7 Hz, $^3J_{P''H}$=11.7 Hz) are obtained, the concentration of which is about 90% and wherefrom the corresponding acid can be liberated with acid treatment.

For instance the following phosphoryl (dichloromethylene)bisphosphonates and their quaternary ammonium salts can be prepared analogously:

P,P-Dimethyl-P'-di-isopropylphosphoryl (dichloromethylene)bisphosphonate methyltributyl ammonium salt, $^{31}$P-NMR (CDCl$_3$): 14.95 ppm (P), −4.84 ppm (P'), −13.98 ppm (P"), $^2J_{PP'}$=20.6 Hz, $^2J_{P'P''}$=26.1 Hz, $^3J_{PH}$=10.6 Hz, $^3J_{P''H}$=7.8 Hz.

P,P-Di-isopropyl-P'-dimethylphosphoryl (dichloromethylene)bisphosphonate N-isopropylpyridinium salt, $^{31}$P-NMR (CDCl$_3$): 9.22 ppm (P), −3.74 ppm (P'), −9.25 ppm (P"), $^2J_{PP'}$=22.3 Hz, $^2J_{P'P''}$=27.4 Hz.

P,P-Di(trimethylsilyl)-P'-di(trimethylsilyl)phosphoryl (dichloromethylene)bisphosphonate methyltributyl ammonium salt, $^{31}$P-NMR (CDCl$_3$): −7.38 ppm (P), −4.51 ppm (P'), −29.00 ppm (P"), $^2J_{PP'}$=24.2 Hz, $^2J_{P'P''}$=22.6 Hz.

EXAMPLE 3

P,P,P'-Trimethyl-P'-pivaloyl(dichloromethylene)bisphosphonate 2.9 g (0.01 moles) P,P,P'-trimethyl(dichloromethylene)bisphosphonate and 1.7 g (0.014 moles) of pivaloylchloride are dissolved in 50 ml of anhydrous acetonitrile and the solution is stirred under reflux for about 1.5 h (the progress of the reaction is followed by $^{31}$P-NMR). The solvent and the excess reagents are evaporated under vacuum, whereby about 3.3 g (90% of the theoretical) of brownish, oily P,P,P'-trimethyl-P'-pivaloyl(dichloromethylene)bisphosphonate are obtained ($^{31}$P-NMR (CDCl$_3$): 10.41 ppm (P), 9.17 ppm (P'), $^2J_{PP'}$=23.7 Hz, $^3J_{PH}$=10.9 Hz, $^3J_{P'H}$=10.9 Hz).

For instance the following (dichloromethylene)bisphosphonic acid P,P,P'-triester-P-monoanhydrides can be prepared analogously:

P,P,P'-Tri-isopropyl-P'-pivaloyl(dichloromethylene)bisphosphonate ($^{31}$P-NMR (CDCl$_3$): 6.40 ppm (P), 4.71 ppm (P'), $^2J_{PP'}$=26.2 Hz, $^3J_{PH}$=6.5 Hz, $^3J_{P'H}$=6.7 Hz).

P,P,P'-Tri-isopropyl-P'-methanesulphonyl (dichloromethylene)bisphosphonate ($^{31}$P-NMR (CDCl$_3$): 5.32 ppm (P), 0.39 ppm (P'), $^2J_{PP'}$=24.8 Hz, $^3J_{PH}$=6.4 Hz, $^3J_{P'H}$=6.8 Hz).

P,P-Dimethyl-P'-trimethylsilyl-P'-pivaloyl (dichloromethylene)bisphosphonate ($^{31}$P-NMR (CDCl$_3$): 12.59 ppm (P), −2.10 ppm (P'), $^2J_{PP'}$=22.7 Hz, $^3J_{PH}$=11.0 Hz).

EXAMPLE 4

P-Methyl-P'-monomethylphosphoryl(dichloromethylene)bisphosphonate dipiperidinium-methyltributyl Ammonium Salt and Free Acid 2.9 g (0.005 moles) of P,P-dimethyl-P'-dimethylphosphoryl(dichloromethylene)bisphosphonate methyltributyl ammonium salt and 12 ml of anhydrous piperidine are mixed for about 1 h at about 80° C. (the progress of the reaction is followed with $^{31}$P-NMR) and the excess piperidine is evaporated under vacuum, whereby 3.5 g (97% of the theoretical) of brownish P-methyl-P'-methylphosphoryl(dichloromethylene)bisphosphonate dipiperidinium-methyltributyl ammonium salt ($^{31}$P-NMR (CDCl$_3$): 7.00 ppm (P), −0.89 ppm (P'), −7.51 ppm (P") $^2J_{PP'}$=16.7 Hz, $^2J_{P'P''}$=28.9 Hz, $^3J_{PH}$=10.0 Hz, $^3J_{P''P}$=11.5 Hz) are obtained, the concentration of which is about 90% and wherefrom the corresponding acid can be liberated with acid treatment.

EXAMPLE 5

P,P-Dimethyl-P',P'-bis(trichloroacetyl)(dichloromethylene)bisphosphonate 4.86 g (0.01 moles) of P,P,P-trimethyl(dichloromethylene)bisphosphonate methyltributyl ammonium salt and 3.64 g (0.02 moles) of trichloroacetylchloride in 50 ml of anhydrous acetonitrile are stirred under reflux for 2 h and the solvent is evaporated under vacuum, whereby about 8 g of oily evaporation residue is obtained, which residue contains about 1:1 P,P-dimethyl-P',P'-di(trichloroacetyl) (dichloromethylene)bisphosphonate ($^{31}$P-NMR (CDCl$_3$): 14.25 ppm (P), 0.11 ppm (P), $^2J_{PP'}$=20.3 Hz, $^3J_{PH}$=10.6 Hz) and P,P-dimethyl-P'-trichloroacetyl(dichloromethylene)bisphosphonate methyltributyl ammonium salt (cf. Ex. 1.).

EXAMPLE 6

P-Methyl-P'-acetyl(dichloromethylene)bisphosphonate Disodium Salt and Free Acid 3.9 g (0.01 moles) of P-methyl(dichloromethylene)bisphosphonate disodium-piperidinium salt and 40 ml of acetanhydride are stirred at room temperature for about 2 days. The mixture is cooled in ice water and the precipitate is filtered and washed with acetone and dried, whereby about 3.3 g (96% of the theoretical) of colourless, crystalline P-methyl-P'-acetyl(dichloromethylene)bisphosphonate disodium salt are obtained ($^{31}$P-NMR (D$_2$O): 9.03 ppm (P), 4.01 ppm (P'), $^2J_{PP'}$=16.5 Hz, $^3J_{PH}$=10.4 Hz), the concentration of which is about 100% and wherefrom the corresponding acid can be liberated with acid treatment.

For instance the following symmetrical (dichloromethylene)bisphosphonate esteranhydrides and their salts can be prepared analogously:

P-Methyl-P'-pivaloyl(dichloromethylene)bisphosphonate bis(diethylammonium) salt, $^{31}$P-NMR (CDCl$_3$): 5.68 ppm (P), 1.78 ppm (P'), $^2J_{PP'}$=25.1 Hz , $^3J_{PH}$=9.9 Hz.

EXAMPLE 7

P,P'-Diacetyl(dichloromethylene)bisphosphonate Disodium Salt and Free Acid 6.7 g (0.02 moles)(dichloromethylene)bisphosphonic acid tetrasodium salt and 220 ml of acetanhydride are stirred for 60 h at about 60° C. (the progress of the reaction is followed with $^{31}$P-NMR) and cooled. The precipitate is filtered and washed with acetone and recrystallized from water-ethanol. After drying about 7.1 g (95% of the theor.) of colourless, crystalline P,P'-diacetyl(dichloromethylene)bisphosphonate disodium salt are obtained ($^{31}$P-NMR (D$_2$O): 2.84 ppm (P ja P')), the concentration of which is about 100% and wherefrom the corresponding acid can be liberated with acid treatment.

For instance the following symmetrical (dichloromethylene)bisphosphonic acid dianhydrides can be prepared analogously:

P,P'-Dibutyroyl(dichloromethylene)bisphosphonate disodium salt, $^{31}$P-NMR (D$_2$O): 2.90 ppm (P ja P').

P,P'-Divaleroyl(dichloromethylene)bisphosphonate disodium salt, $^{31}$P-NMR (D$_2$O): 3.13 ppm (P ja P').

P,P'-Di(pivaloyl)(dichloromethylene)bisphosphonate disodium salt, $^{31}$P-NMR (D$_2$O): 3.74 ppm (P ja P').

P,P'-Di(benzoyl)(dichloromethylene)bisphosphonate disodium salt, $^3$P-NMR (D$_2$O): 3.85 ppm (P ja P').

P,P'-Di(isobutyroyl)(dichloromethylene)bisphosphonate disodium salt, $^{31}$P-NMR (D$_2$O): 2.75 ppm (P ja P').

P,P'-Dihexanoyl(dichloromethylene)bisphosphonate disodium salt, $^{31}$P-NMR (D$_2$O): 3.03 ppm (P ja P').

EXAMPLE 8

P,P-Bis(diethylamido)-P'-ethoxycarbonyl) dichloromethylene)bisphosphonate Methyltributyl Ammonium Salt and Free Acid 1.895 g (0.003 moles) P,P-bis(diethylamido)-P'-methyl (dichloromethylene)bisphosphonate methyltributyl ammonium salt were dissolved in 11 ml of dry acetonitrile. The mixture was heated with a jacket and stirred until inside temperature was 80° C. To the mixture was dropped at 80° C. during 15 minutes a solution, which contained 355 mg (0.003 moles) of ethylchloroformate in 11 ml of dry acetonitrile. The mixture was stirred for 3 h 45 min while inside temperature was 80–82° C. and evaporated to dryness. It was left crystallizing overnight, whereby 2.1 g of P,P-bis (diethylamido)-P'-ethoxycarbonyl(dichloromethylene) bisphosphonate methyltributyl ammonium salt (31P-NMR (D$_2$O): 27.11 ppm (P), 0.73 ppm (P'), $^2J_{PP'}$=22.3 Hz), were obtained, the concentration of which is about 90% and wherefrom the corresponding acid can be liberated with acid treatment.

EXAMPLE 9

P,P-Di(ethoxycarbonyl)dichloromethylene)bisphosphonate di(methyltributylammonium) Salt and Free Acid 3.36 g (0.005 moles) P,P'-dimethyl(dichloromethylene) bisphosphonate di(methyltributylammonium) salt were dissolved in 20 ml of anhydrous acetonitril, to the solution was added 2.17 g (0.02 moles) of ethylchloroformate and it was mixed for 30 min at about 75° C. The solvent was evaporated under vacuum, whereby about 5.03 g (95% of the theoretical) of oily P,P'-di(ethoxycarbonyl) (dichloromethylene)bisphosphonate di(methyltributylammonium) salt are obtained ($^{31}$P-NMR (CDCl$_3$): 0.40 ppm (P ja P')), the concentration of which is about 85% and wherefrom the corresponding acid can be liberated with acid treatment.

For instance the following symmetrical (dichloromethylene)bisphosphonate dianhydrides can be prepared analogously:

P,P'-Bis (dimethylcarbonyl)(dichloromethylene) bisphosphonate disodium salt ($^{31}$P-NMR D$_2$O): 2.53 ppm (P ja P')).

EXAMPLE 10

P,P-Dimethyl-P'-pivaloyl-P-trimethylsilyl (dichloromethylene)bisphosphonate 2.2 g (0.004 moles) of P,P-dimethyl-P'-pivaloyl (dichloromethylene)bisphosphonate methyltributyl ammonium salt are dissolved in 20 ml of anhydrous acetonitrile and the solution is cooled to 0° C. and 0.45 g (0.0042 moles) of chlorotrimethylsilane in 5 ml of anhydrous acetonitrile are added while stirring at 0–5° C. After addition, the mixture is stirred for 10 min at 0–5° C. and for 1 h without cooling and the solvent is evaporated under vacuum, whereby the desired product is obtained as brown oil with a degree of purity of about 80%. ($^{31}$P-NMR (CDCl$_3$): 12.59 ppm (P), −2.10 ppm (P'), $^2J_{PP'}$=22.7 Hz, $^3J_{PH}$=11.0 Hz).

EXAMPLE 11

P,P'-Di(tetradecanoyl)(dichloromethylene)bisphosphonate Dipyridinium Salt 1.0 g (4.08 mmol) of (dichloromethylene)bisphosphonic acid and 10 ml of dry tetrahydrofurane are mixed and 2.0 g (8.16 mmol) of tetradecanoylchloride and 1.3 g (16.32 mmol) of dry pyridine are added at about 23° C. The grey suspension is stirred at about 23° C. for 3 h and evaporated to dryness under vacuum. The yield is 4.3 g (100% of the theor.), of which 3.4 g is P,P'-di(tetradecanoyl) (dichloromethylene)bisphosphonate dipyridinium salt ($^{31}$P-NMR(CDCl$_3$): 1.65 ppm (P ja P')), the concentration of which is about 100% ($^{32}$P-NMR), and 0.9 g is pyridiniumhydrochloride.

Analogously has been prepared also:

P,P'-Di(octadecanoyl)(dichloromethylene) bisphosphonate dipyridinium salt, $^{31}$P-NMR (CDCl$_3$): 1.60 ppm (P ja P').

EXAMPLE 12

Monohexanoyloxy(dichloromethylene)bisphosphonate Trisodium Salt 5.0 g (15.0 mmol) of (dichloromethylene)bisphosphonate tetrasodium salt and 23.1 g (108.2 mmol) of hexanoic acid anhydride are mixed at about 85° C. for 7 h and at room temperature for about 18 h (the progress of the reaction is followed with $^{31}$P-NMR). The mixture is filtered and washed with 2 ml of acetone and dried under vacuum, whereby about 5.4 g (88% of the theor.) of crystalline monohexanoyloxy(dichloromethylene)bisphosphonate trisodium salt ($^{31}$P-NMR (D$_2$O): 7.57 ppm (P), 4.59 ppm (p), $^2J_{PP}$=17.6 Hz) are obtained with a concentration of 81%, while concentration of the starting material is 16% and the concentration of P,P'-dihexanoyloxy(dichloromethylene) bisphosphonate disodium salt is 3% ($^{31}$P-NMR).

EXAMPLE 13

In Vitro Tests of Prodrug Molecules

HPLC Method Used in the In Vitro Tests

Clodronate and the prodrug molecules of clodronate were analysed with reverse phase/ion pair HPLC method (an isocratic program for clodronate; a gradient program for the simultaneous analysis of clodronate and a prodrug molecule), where detection of compounds was based on the measurement of light scattering caused by unevaporated compounds.

Equipment: Merck LaChrom HPLC (Merck Hitachi Ltd., Japan) Kromasil 100 RP-C8 (250×4.6 i.d., 5 µm) (Higgins Analytical Inc., USA)

Eluent:

Isocratic programe: methanol/ammoniumacetate buffer (3:97, pH 4.6), which contained 2.25% butylamine as ion pair reagent, flow 1.2 ml/min.

Gradient program: methanol (3%→40–60% during 1 min–6 min)/ammoniumacetate (pH 4.6), which contained 2.25% butylamine as ion pair reagent, flow 1.2 ml/min.

Detector: Sedex 55 light scattering detector (Sedere, France)

Settings: temperature of detector 70° C., pressure of evaporating gas (filtered air) 2.2 bar.

Water-solubility of Prodrug Molecules

Water-solubilities of prodrug molecules were determined in phosphate buffer (50 mM, pH 7.4) at room temperature.

An excess of the compound to be tested was dissolved in about 5 ml of phosphate buffer. The suspension was stirred for 2 hours, the suspension was filtered, and the prodrug concentration of the filtrate was determined with HPLC. Water-solubility of clodronate was determined with the same method. Water-solubilities of the compounds to be tested are shown in Table 1.

TABLE 1

Water-solubilities of clodronate and its prodrug molecules at pH 7.4.

| Prodrug | Water-solubility (mg/ml) |
| --- | --- |
| Clodronate | 397 |
| Acetic acid dianhydride (Ex. 7) | 190 |
| Butanoic acid dianhydride (Ex. 7) | 172 |
| Pivalyl acid dianhydride (Ex. 7) | 23,5 |
| Benzoe acid dianhydride (Ex. 7) | 6,0 |

Distribution Coefficient of Prodrug Molecules

The fat-solubility of the compounds of the test was studied by determining the distribution coefficients (P) of the compounds at pH 7.4 and 2.0. The analysis were carried out in a mixture of octanol and buffer.

When the octanol/buffer method of analysis was used, 1-octanol and the phosphate buffer used (50 mM, pH 7.40, $\mu$=0.15) were saturated with each other by stirring a mixture of these overnight. Phases were separated and a prodrug standard solution with the desired concentration was made in the buffer phase. Appropriate volumes of 1-octanol and the standard solution of phosphate buffer were mixed and the mixture was shaken vigorously for 60 min. After shaking the phases were separated and the concentration of the compound to be studied was analysed from the buffer phase before and after distribution according to the above described HPLC method. Distribution coefficient P was calculated from the following formula:

$$P = \left(\frac{C_i - C_a}{C_a}\right)\left(\frac{V_a}{V_o}\right)$$

where
- $C_i$=concentration of the compound to be studied before distribution
- $C_a$=concentration of the compound to be studied after distribution
- $V_a$=volume of the buffer phase
- $V_o$=volume of the octanol phase The distribution coefficient values (log P) of the prodrug molecules to be studied are shown in Table 2.

TABLE 2

Distribution coefficients of prodrug molecules to be studied

| Prodrug | Log P (pH 7.4) | Log P (pH 2.0) |
| --- | --- | --- |
| Acetic acid dianhydride (Ex. 7) | −2.2 | −1.4 |
| Butanoic acid dianhydrid (Ex. 7) | −2.4 | −1.9 |
| Pivalyl acid dianhydride (Ex. 7) | −2.3 | −2.0 |
| Benzoe acid dianhydrid (Ex. 7) | −2.4 | −1.5 |

Note: The distribution coefficient of clodronate cannot be determined with the method in question, because clodronate is extremely water-soluble (log P value of the monoethyl ester of clodronate is −5.4 (J Med Chem 34: 2338–2343, 1991)).

Chemical Hydrolysis of Prodrug Molecules

Chemical hydrolysis of prodrug molecules was analysed in phosphate buffer (50 mM, $\mu$=0.15) at pH 2.0 and 7.4 and at 37° C.

The compound to be studied was dissolved in 10.0 ml of phosphate buffer. The solution was stirred for 24–1000 h in a water bath with a magnetic stirrer, and samples were taken at regular intervals and analysed with HPLC. From the results a graph of pseudo I order was drawn, where the amount of the remaining compound was shown as a function of time. From the slope (kk) of the linear graph so obtained, a dissociation constant k (k=2.303×−kk) was calculated, wherefrom the half-life T½ ($T_{1/2}$=0.693/k) of the prodrug molecule under the circumstances in question was calculated. The half-lives of the compounds to be tested are shown in Table 3.

Enzymatic Hydrolysis of Prodrug Molecules (in Plasma)

The enzyme hydrolysis rate of prodrug molecules was determined in a plasma/buffer mixture (80%–20%) at pH 7.40 and at 37° C.

The compound to be tested was dissolved in the buffer part and, after dissolution, plasma with a temperature of 37° C. was added. The solution was stirred with a magnetic stirrer and a sample of 0.25 ml was taken from the mixture at intervals of 1–360 min (depending on the molecule to be tested), to which sample 0.25 ml methanol (denatures proteins) was added. The sample was centrifuged, the clear supernatant was evaporated to dryness, the residue was dissolved in the eluent of the HPLC method, and the remaining prodrug concentration and the amount of the clodronate formed were analysed with HPLC. From the concentrations obtained a first-order graph was drawn (the remaining prodrug amount as a function of time), wherefrom a dissociation constant and half-life (T½) were determined. The half-lives of the compounds to be tested are shown in Table 3.

TABLE 3

Half-lives of the prodrug molecules in buffer solution (pH 2.0 and 7.4) and in 80% plasma (pH 7.4) at 37° C.

| Prodrug | T½ pH 2.0 | T½ pH 7.4 | T½ Plasma |
| --- | --- | --- | --- |
| Acetic acid dianhydride (Ex. 7) | 0.7 h | 15.2 h | 1) |
| Butanoic acid dianhydride (Ex. 7) | 0.8 h | 31.3 h | 2) |
| Pivalyl acid dianhydride (Ex. 7) | 8.6 h | 790 h | 3.3 ± 0.6 h |
| Benzoe acid dianhydrid (Ex. 7) | 286 h | 235 h | 3) |

1) In the first sample (1 minute), 101.6 ± 1.2% (mean ± SE, n = 3) of clodronate had been released.
2) In the first sample (1 minute), 98.0 ± 6.9% (mean ± SE, n = 3) of clodronate had been released.
3) In the first sample (1 minute), 91.4 ± 8.6% (mean ± SE, n = 3) of clodronate had been released.

EXAMPLE 14

Effect on PTH-induced bone resorption in vitro and the absorption and hydrolysis of the compounds in vivo Effect on PTH-induced Bone Resorption in Mouse Calvaria Newborn mice were labeled by a subcutaneous injection of $^{45}$Ca four days prior to sacrifice. Calvarial bone fragments were microdissected from the parietal bones, preincubated in culture medium with indomethacin, washed and then cultured for three days with and without a bisphosphonate prodrug. Bone resorption was stimulated by parathyroid hormone (PTH, 10 nM), and the effect on this stimulated resorption was measured. As presented in Table 4, an inhibition of resorption by the compounds was shown. The inhibition by the bisphosphonate prodrugs was even higher than with the parent drug.

TABLE 4

Inhibition of PTH-induced bone resorption

| Compound | Concentration μmol/l | Inhibition of resorption 100 (PTH-x)/PTH, % |
|---|---|---|
| 1 | 100 | 48,7 |
| 2 | 100 | 64,8 |
| 3 | 100 | 50,5 |
| 4 | 100 | 53,9 |
| Clodronate (parent drug) | 100 | 43,2 |

Compound 1=Acetic acid dianhydride (P,P'-diacetyl (dichoromethylene)bisphosphonate disodium salt)
Compound 2=P,P-di(isobutyroyl)(dichloromethylene) bisphosphonate disodium salt
Compound 3=P,P'-di(tetradecanoyl)(dichoromethylene) bisphosphonate disodium salt
Compound 4=P,P'-di(octadecanoyl)(dichoromethylene) bisphosphonate disodium salt
Clodronate=dichloromethylenebisphosphonic acid disodium salt Absorption and Hydrolysis In Vivo Absorption and hydrolysis of the compounds in vivo was studied in fasted rats. Absorption was determined from the total amount excreted into urine during 72 hours after administration. For the determination of oral bioavailability excreted amount after oral administration was compared with that after intravenous administration. The urine samples were analyzed for the parent drug with mass-selective or nitrogen phosphorous-detection gas chromatography. The results presented in Table 5 show increased bioavailability of the bisphosphonate prodrugs compared with that of the parent compound.

TABLE 5

Absorption of the bisphosphonate prodrugs

| Compound, dose 100 μmol/kg | Bioavailability, % |
|---|---|
| 1 | 4.5 |
| 2 | 8.78 |
| 3 | 4.18 |
| 4 | 23.37 |
| Clodronate (parent compound) | 2.17 |

Compounds are the same as in Table 4.

What is claimed is:

1. A methylenebisphosphonic acid anhydride derivative having the formula I

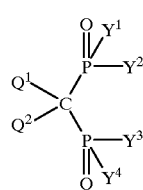

(I)

wherein $Y^1$ and $Y^3$ are a $OCOR^1$ group;

$Y^2$ and $Y^4$ are a $OR^1$ group, wherein $R^1$, is a hydrogen, a straight, or branched, $C_1$–$C_{22}$ alkyl or phenyl;

$Q^1$ and $Q^2$ are independently of each other hydrogen, fluorine, chlorine, bromine or iodine, geometrical isomers, optically active isomers, of the compound, or a pharmacologically acceptable salt of the compound.

2. The methylenebisphosphonic acid anhydride derivative according to claim 1, wherein $Q^1$ and $Q^2$ in the formula I are both chlorine.

3. The methylenebisphosphonic acid anhydride derivative according to claim 1, wherein it is P,P'-diacetyl (dichloromethylene)bisphosphonate disodium salt or free acid, P,P'-dibutyroyl(dichloromethylene)bisphosphonate disodium salt or free acid, P,P'-di(pivaloyl) (dichloromethylene)bisphosphonate disodium salt or free acid, P,P'-di(benzoyl)(dichloromethylene)bisphosphonate disodium salt or free acid, P,P'-di(isobutyroyl) (dichloromethylene)bisphosphonate disodium salt or free acid, P,P'-di(tetradecanoyl)(dichloromethylene) bisphosphonate disodium salt or free acid, or P,P'-di (octadecanoyl)(dichloromethylene)bisphosphonate disodium salt or free acid.

4. Process for preparing methylenebisphosphonic acid anhydride derivatives according to claim 1, or a pharmacologically acceptable salt thereof wherein, a) a starting compound according to formula II, wherein at least one of the group $X^1$–$X^4$ or all are independently of each other OH or OM, where M can be a metal or ammonium group, and $Q^1$ and $Q^2$ are hydrogen or halogen, is selectively reacted with a desired acid derivative Z-A, wherein A means a group $OCOR^1$ and Z is halogen or analog; or

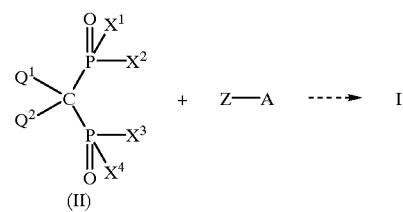

(II)

b) a starting material according to formula II, wherein at least one of the groups $X^1$–$X^4$ or all are independently of each other halogen or a halogen analog, is reacted with a selected acid or with selected acids (A-OH) (Z=OH) or with its metal salt (A-OM) (Z=OM), wherein A and M have the same meanings as in paragraph a), and finally the extra groups X and optionally extra groups Y are removed for example by hydrolyzing with water; or c) for the preparation of tri-, di- and mono-partial anhydride derivatives I, under paragraphs a) or b) above obtained tetraanhydrides are selectively hydrolyzed.

5. A pharmaceutical preparation, comprising:

a methylenebisphosphonic acid anhydride derivative of the formula I according to claim 1 or a pharmacologically acceptable salt thereof, and a pharmaceutically acceptable carrier.

* * * * *